(12) United States Patent
Roh

(10) Patent No.: US 11,523,787 B2
(45) Date of Patent: Dec. 13, 2022

(54) DIGITAL BREAST TOMOSYNTHESIS DEVICE CAPABLE OF CONTROLLING POSITION OF X-RAY FOCUS

(71) Applicants: MEDI-FUTURE, INC., Seongnam-si (KR); Young Sup Roh, Seongnam-si (KR)

(72) Inventor: Young Sup Roh, Seongnam-si (KR)

(73) Assignees: MEDI-FUTURE, INC.; Young Sup Roh

( * ) Notice: Subject to any disclaimer, the term of this patent is extended or adjusted under 35 U.S.C. 154(b) by 0 days.

(21) Appl. No.: 17/057,822

(22) PCT Filed: May 17, 2019

(86) PCT No.: PCT/KR2019/005963
§ 371 (c)(1),
(2) Date: Nov. 23, 2020

(87) PCT Pub. No.: WO2019/225915
PCT Pub. Date: Nov. 28, 2019

(65) Prior Publication Data
US 2021/0298705 A1 Sep. 30, 2021

(30) Foreign Application Priority Data
May 23, 2018 (KR) .......................... 10-2018-0058289

(51) Int. Cl.
*A61B 6/00* (2006.01)
*A61B 6/02* (2006.01)
(52) U.S. Cl.
CPC .............. *A61B 6/502* (2013.01); *A61B 6/025* (2013.01); *A61B 6/4021* (2013.01); *A61B 6/4441* (2013.01)

(58) Field of Classification Search
CPC .............................. A61B 6/005; A61B 6/4021
See application file for complete search history.

(56) References Cited

U.S. PATENT DOCUMENTS

| 8,345,818 B2 | 1/2013 | Jung |
| 10,206,644 B2 | 2/2019 | Kim |

(Continued)

FOREIGN PATENT DOCUMENTS

| CN | 108836373 A | 11/2018 |
| KR | 10-1174351 | 8/2012 |

(Continued)

OTHER PUBLICATIONS

Extended European Search Report 19807629.1-1126 dated Feb. 18, 2022.

*Primary Examiner* — Dani Fox
(74) *Attorney, Agent, or Firm* — The Belles Group, P.C.

(57) ABSTRACT

Disclosed is a digital breast tomosynthesis system including: an X-ray tube configured to generate X-rays; a C-arm configured to receive the X-ray tube and rotate about a first rotation axis during an X-ray exposure period; an X-ray detector configured to convert the X-ray, which is emitted from the X-ray tube and passes through a breast, into image information; and a focal spot controller configured to operate in conjunction with a movement of the X-ray tube caused by a rotation of the C-arm, in which the focal spot controller controls a position of a focal spot of the X-ray with various methods. As a result, the position of the focal spot of the X-ray tube may be controlled by the simple structure and method, thereby eliminating blurring of a projection image that affects the determination of quality of a three-dimensional image, and thus significantly improving sharpness.

9 Claims, 7 Drawing Sheets

(56) References Cited

U.S. PATENT DOCUMENTS

| | | |
|---|---|---|
| 10,561,387 B2 | 2/2020 | Smith |
| 2010/0303202 A1 * | 12/2010 | Ren .................... A61B 6/4021 |
| | | 378/62 |
| 2010/0303207 A1 | 12/2010 | Tsujii et al. |
| 2011/0188624 A1 | 8/2011 | Ren et al. |

FOREIGN PATENT DOCUMENTS

| | | |
|---|---|---|
| KR | 1020130058633 | 6/2013 |
| KR | 10-1457099 | 10/2014 |
| KR | 10-2016-0071938 | 6/2016 |
| KR | 10-1787714 | 10/2017 |
| KR | 10-1836549 | 3/2018 |

\* cited by examiner

[FIG. 1]
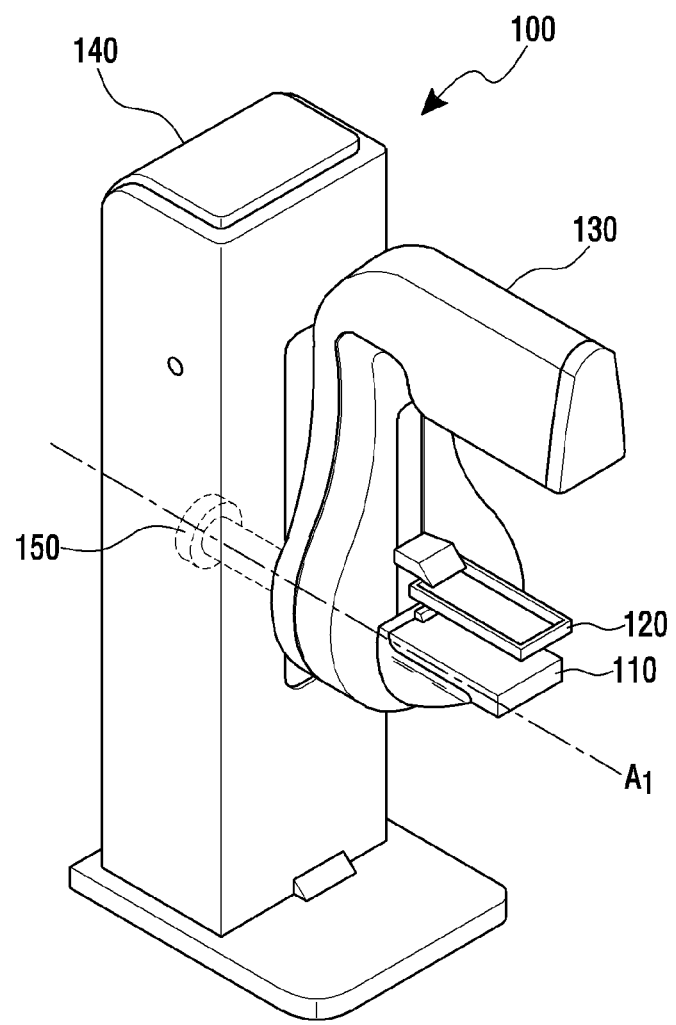

[FIG. 2]
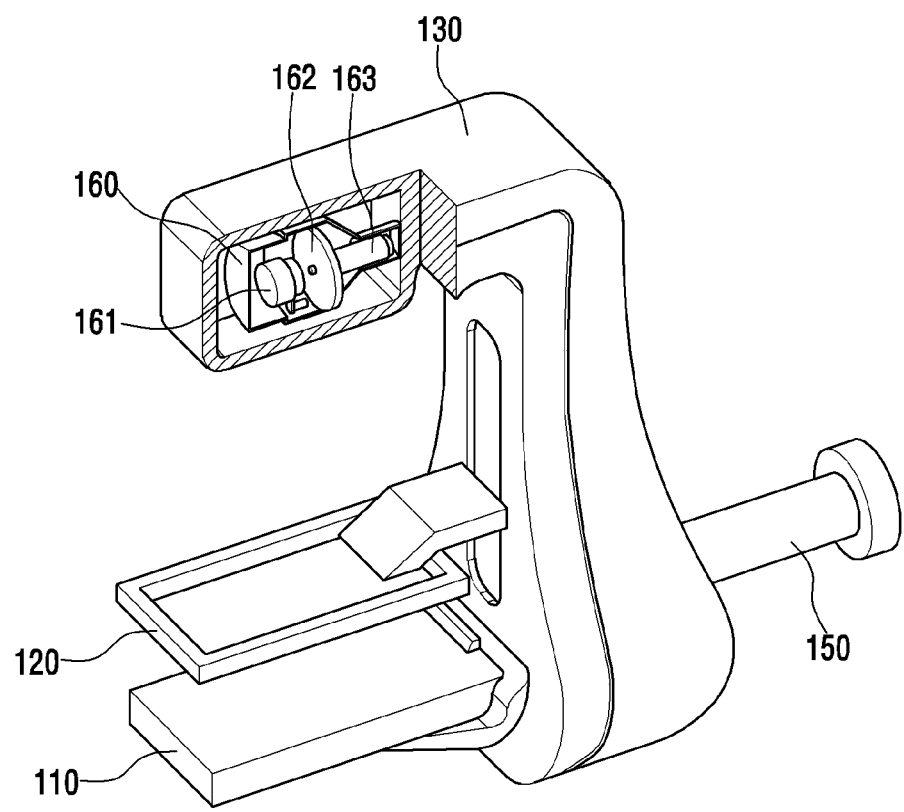

[FIG. 3]
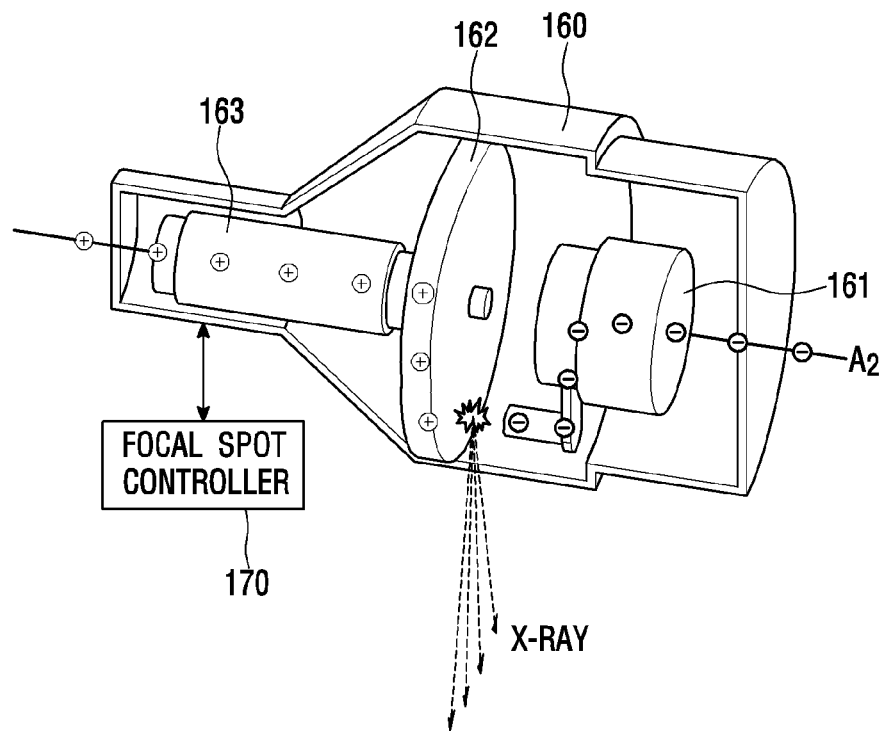
[FIG. 4]
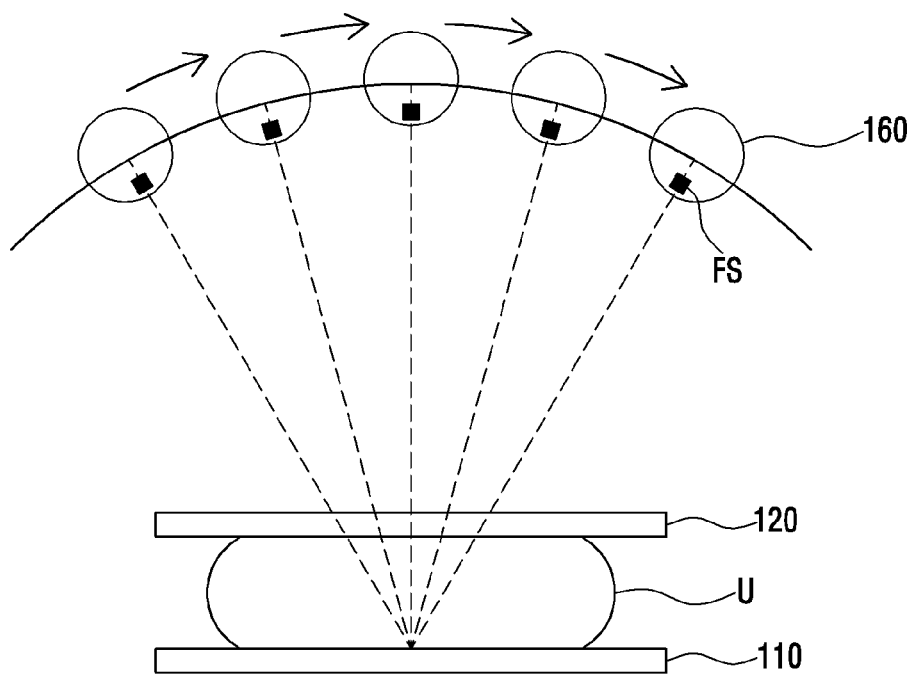

[FIG. 5]
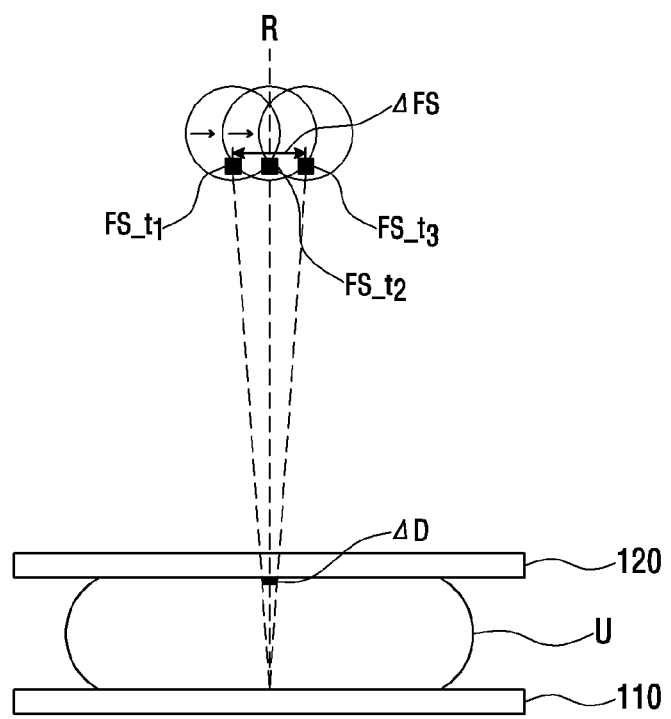

[FIG. 6]
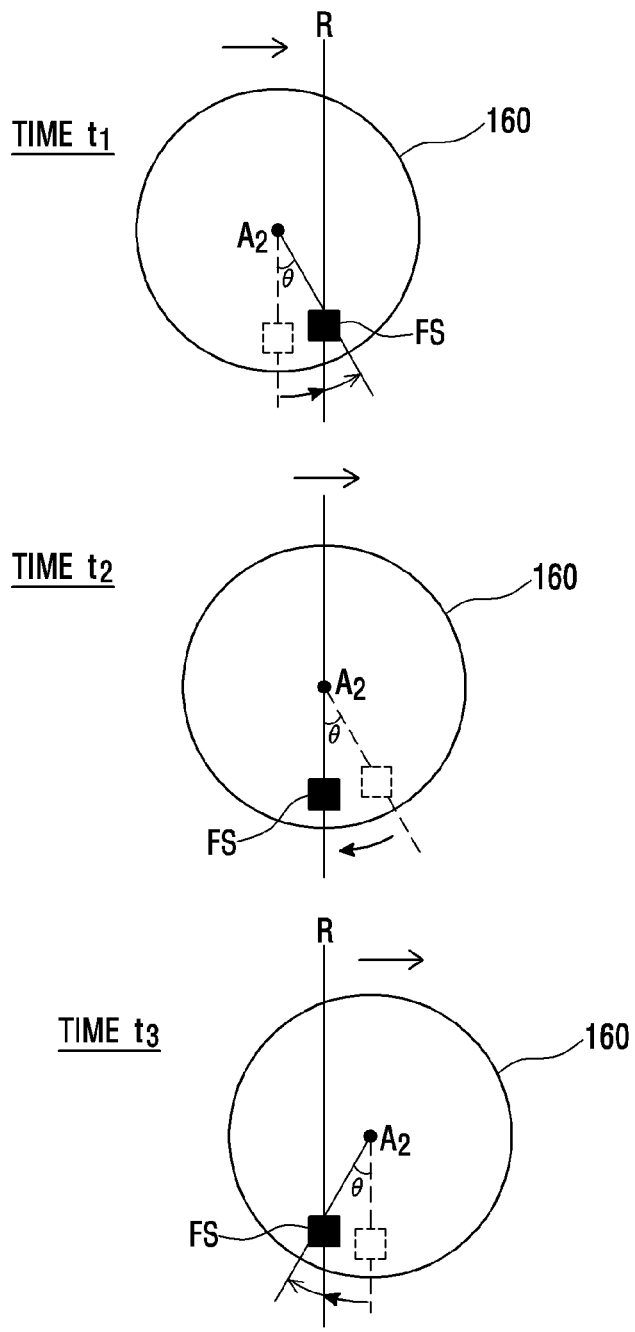

[FIG. 7]
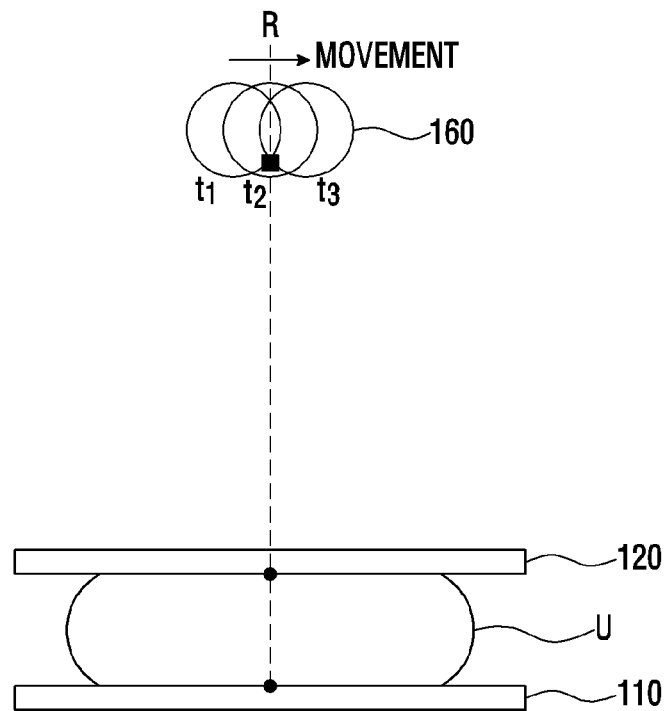
[FIG. 8]
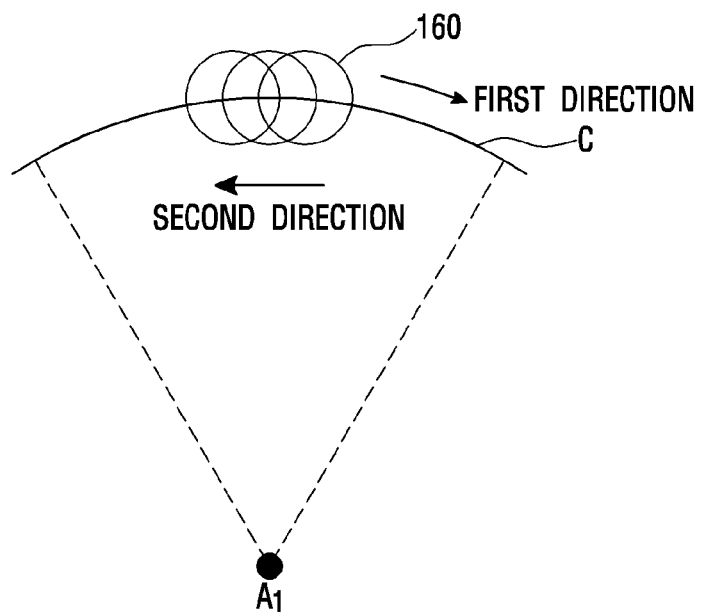

[FIG. 9]
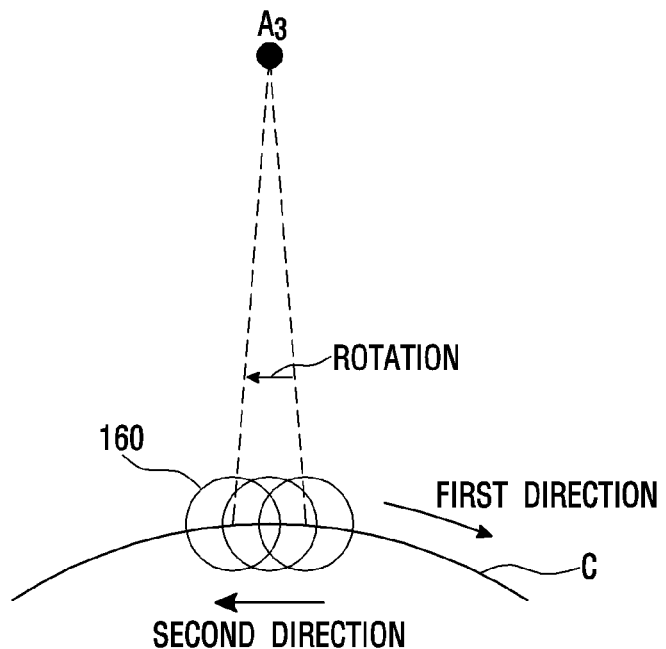

DIGITAL BREAST TOMOSYNTHESIS DEVICE CAPABLE OF CONTROLLING POSITION OF X-RAY FOCUS

CROSS-REFERENCE TO RELATED PATENT APPLICATIONS

The present application is a U.S. national stage application under 35 U.S.C. § 371 of PCT Application No. PCT/KR2019/005963, filed May 17, 2019, which claims priority to Korean Patent Application No. 10-2018-0058289, filed May 23, 2018. The disclosures of the aforementioned priority applications are incorporated herein by reference in their entireties.

TECHNICAL FIELD

The present invention relates to a digital breast tomosynthesis system capable of controlling a position of a focal spot of an X-ray, and more particularly, to a digital breast tomosynthesis system capable of improving blurring by constantly maintaining a spatial position of a focal spot of an X-ray.

BACKGROUND ART

Cancers caused by infinite proliferation of cells include liver cancer, colorectal cancer, gastric cancer, and lung cancer. In particular, breast cancer that affects women is a very fatal disease and requires periodic diagnosis and management. An incidence rate of breast cancer in Asia is increasing due to westernized eating habits. Therefore, many countries recommend women over a certain age to be tested for breast cancer at regular intervals.

Methods of diagnosing breast cancer include breast ultrasonography and breast magnetic resonance imaging (MRI), but mammography using X-rays is representatively used. The mammography acquires X-ray images of breasts from an image receptor after exposure to an appropriate dose of X-rays through an automatic exposure control (AEC) device.

The acquisition of the X-ray images of the breasts is generally performed by full field digital mammography (FFDM), digital breast tomosynthesis (DBT), or breast computed tomography (BCT). The FFDM acquires a two-dimensional image, the DBT implements a three-dimensional image by reconstructing an acquired projection image by rotating an X-ray generator, and the BCT implements a three-dimensional image by rotating an X-ray generator and an X-ray detector.

In the case of the DBT for acquiring the three-dimensional image, the X-ray tube rotates about the breast to acquire a projection image. In this case, because the X-ray tube moves consistently, blurring is caused by the movement of the focal spot. For this reason, the acquired projection image inevitably has lower sharpness than an actual image, and a three-dimensional image finally acquired by performing 3D image reconstruction by using the acquired projection image inevitably has low quality.

In order to solve this problem, various methods have been used. For example, there has been proposed a method of controlling a position of a focal spot of an X-ray tube that moves to acquire a projection image. However, most of the methods have used means for changing a gradient of a positive electrode constituting the X-ray tube, moving a focusing cup of a negative electrode, or using a lens. These means need to individually control respective elements constituting the X-ray tube, which causes a problem in that it is not easy to implement a system, a precise control device is required, and a large amount of costs is incurred.

DISCLOSURE

Technical Problem

The present invention has been contrived in consideration of the above-mentioned problems, an object of the present invention is to provide a digital breast tomosynthesis system capable of controlling a position of a focal spot of an X-ray tube with a simple method in order to improve sharpness of a projection image that affects determination of quality of a three-dimensional image.

Technical Solution

In order to achieve the above-mentioned object, a digital breast tomosynthesis system according to an exemplary embodiment of the present invention includes: an X-ray tube configured to generate X-rays; a C-arm configured to receive the X-ray tube and rotate about a first rotation axis during an X-ray exposure period; an X-ray detector configured to convert the X-ray, which is emitted from the X-ray tube and passes through a breast, into image information; and a focal spot controller configured to operate in conjunction with a movement of the X-ray tube caused by a rotation of the C-arm, the focal spot controller being configured to control a position of a focal spot of the X-ray by rotating the X-ray tube about a second rotation axis in the C-arm.

Further, as a position of the focal spot is moved in a direction opposite to a movement direction of the X-ray tube by the rotation about the second rotation axis, a spatial position of the focal spot based on the X-ray detector may be fixed.

In addition, the focal spot controller may calculate a rotation angle, at which a spatial position of the focal spot is fixed, based on a movement speed of the X-ray tube, and rotate the X-ray tube based on the calculated rotation angle.

Further, the second rotation axis may be positioned on a circumference having, at a center thereof, the first rotation axis and having a radius which is a distance between the first rotation axis and the X-ray tube.

In addition, the focal spot controller may control and fix a spatial position of the focal spot by rotating the X-ray tube so that the focal spot is advanced from a predetermined position based on a movement direction of the X-ray tube, and then by rotating the X-ray tube again in the opposite direction.

Meanwhile, in order to achieve the above-mentioned object, a digital breast tomosynthesis system according to another exemplary embodiment of the present invention includes: an X-ray tube configured to generate X-rays; a C-arm configured to receive the X-ray tube and rotate about a first rotation axis during an X-ray exposure period; an X-ray detector configured to convert the X-ray, which is emitted from the X-ray tube and passes through a breast, into image information; and a focal spot controller configured to control a position of a focal spot of the X-ray by moving the X-ray tube, which moves in a first direction along a circumference having, at a center thereof, the first rotation axis, in a second direction opposite to the first direction.

Further, the focal spot controller may fix a spatial position of the focal spot based on the X-ray detector by moving the focal spot in the second direction.

Meanwhile, in order to achieve the above-mentioned object, a digital breast tomosynthesis system according to still another exemplary embodiment of the present invention includes: an X-ray tube configured to generate X-rays; a C-arm configured to receive the X-ray tube and rotate about a first rotation axis during an X-ray exposure period; an X-ray detector configured to convert the X-ray, which is emitted from the X-ray tube and passes through a breast, into image information; and a focal spot controller configured to operate in conjunction with a movement of the X-ray tube caused by a rotation of the C-arm, the focal spot controller being configured to control a position of a focal spot of the X-ray by rotating the X-ray tube about a third rotation axis, in which the third rotation axis is positioned inside or outside a circumference having, at a center thereof, the first rotation axis and having a radius which is a distance between the first rotation axis and the X-ray tube.

Further, the focal spot controller may fix a spatial position of the focal spot based on the X-ray detector by rotating the focal spot about the third rotation axis.

Advantageous Effects

According to the digital breast tomosynthesis system having the above-mentioned configuration, the position of the focal spot of the X-ray tube may be controlled by the simple structure and method, thereby eliminating blurring of a projection image that affects the determination of quality of a three-dimensional image, and thus significantly improving sharpness.

DESCRIPTION OF DRAWINGS

FIG. 1 is a perspective view illustrating a digital breast tomosynthesis system according to an exemplary embodiment of the present invention.

FIG. 2 is a cross-sectional view illustrating the digital breast tomosynthesis system according to the present invention which is partially cut out.

FIG. 3 is an enlarged view of an X-ray tube included in the digital breast tomosynthesis system according to the present invention.

FIG. 4 is a view illustrating a method of acquiring projection images in a general breast tomosynthesis system.

FIG. 5 is a view for explaining a problem caused in the related art.

FIG. 6 is a view for explaining focal spot control to be performed by a focal spot controller in the digital breast tomosynthesis system according to the present invention.

FIG. 7 is a view illustrating a state in which the focal spot control has been performed in the digital breast tomosynthesis system according to the present invention.

FIG. 8 is a view for explaining a focal spot control method to be performed by the focal spot controller in the digital breast tomosynthesis system according to the present invention.

FIG. 9 is a view for explaining the focal spot control method to be performed by the focal spot controller in the digital breast tomosynthesis system according to the present invention.

BEST MODE

The present invention will be described in detail with reference to the accompanying drawings illustrating specific exemplary embodiments for carrying out the present invention. The specific exemplary embodiments illustrated in the accompanying drawings will be described in detail so that those skilled in the art to which the present invention pertains may sufficiently carry out the present invention. Exemplary embodiments other than the specific exemplary embodiments are different from one another but need not be mutually exclusive. Further, it should be understood that the following detailed description is not intended to limit the present invention.

The detailed description of specific exemplary embodiments illustrated in the accompanying drawings will be read in connection with the accompanying drawings, and the drawings are regarded as a part of the description of the entire invention. The description of directionality or orientation is merely for convenience of description and is not intended to limit the scope of the present invention in any way.

Specifically, the terms "down, up, horizontal, vertical, upper, lower, upward, downward, above, below, etc.", which indicate positions, or derivatives thereof (e.g., "horizontally, downwardly, upwardly, etc.") should be understood with reference to all the drawings being described and the related descriptions. In particular, since these relative words are merely for convenience of explanation, it is not necessary to configure or operate the device of the present invention in a specific direction.

In addition, unless otherwise stated, the terms "mounted, attached, connected, coupled, interconnected, etc.", which indicate coupling relationships between components, may mean that the individual components are directly or indirectly attached, connected, or fixed, and these terms should be understood as the terms including not only a state in which the components are movably attached, connected, or fixed, but also a state in which the components cannot be moved.

A thickness or a size of each constituent element illustrated in the accompanying drawings is exaggerated, omitted, or schematically illustrated for the purpose of clarity and for convenience of description. That is, a size of each constituent element does not entirely reflect an actual size.

FIG. 1 is a perspective view illustrating a digital breast tomosynthesis system 100 according to the present invention, FIG. 2 is a cross-sectional view illustrating the digital breast tomosynthesis system 100 according to the present invention which is partially cut out, and FIG. 3 is an enlarged view of an X-ray tube 160 included in the digital breast tomosynthesis system 100 according to the present invention.

As illustrated in FIG. 1, the digital breast tomosynthesis system 100 according to the exemplary embodiment of the present invention includes an X-ray detector 110, a compression paddle 120, a C-arm 130, a gantry 140, and a rotary part 150.

The X-ray detector 110 has a function of converting an X-ray, which has passed through a breast U, into image information and may also have a function as a bucky on which a patient's breast U is placed. However, another exemplary embodiment may further include a separate configuration for accommodating the X-ray detector 110.

The X-ray detector 110 may be variously configured as various types of detectors such as a screen-film detector, an indirect conversion digital detector, and a direct conversion digital detector. In addition, although not illustrated in FIG. 1, a grid (not illustrated) for removing scattered X-rays may be provided on an upper surface of the X-ray detector 110.

The compression paddle 120 is designed to be movable vertically and provided above the X-ray detector 110. The compression paddle 120 may be made of a material that does not affect the acquisition of X-ray images of the breast U, and the vertical movement of the compression paddle 120 may be controlled so that there is no damage caused by the compression. For example, when compression force equal to or higher than a critical value is applied to the patient's breast U, the compression paddle 120 may be controlled so that the downward movement of the compression paddle 120 is stopped or compression force is reduced. However, in order to acquire a clear projection image, the compression paddle 120 needs to be controlled to apply appropriate compression force so that the patient's breast U is entirely and uniformly spread.

The C-arm 130 may include the X-ray tube 160. Further referring to FIGS. 2 and 3, the X-ray tube 160 basically includes a cathode 161, an anode 162, and a motor 163. The cathode 161 includes a filament, and electrons are emitted to the anode 162 as the filament is heated. The anode 162 is connected to the motor 163 and configured to be rotated, and high-energy electrons emitted from the cathode 161 collide with tungsten atoms of the anode 162 to generate X-ray photons. The X-ray photons emitted from the circular plate-shaped anode 162 are limited in terms of a projection region by a collimator (not illustrated) and discharged through a tube port (not illustrated). In addition, the X-ray tube 160 may further include a filter (not illustrated) or the like.

In a state in which the patient's breast U is placed on the upper surface of the X-ray detector 110 and then the breast U is compressed by the compression pad 120, the X-rays emitted from the X-ray tube 160 pass through the compressed breast U and reach the X-ray detector 110. The X-ray detector 110 generates signals related to positions and incident doses of the X-rays, and this information enables a three-dimensional image of the breast U to be acquired by image reconstruction algorithm.

The C-arm 130 receives therein the X-ray tube 160. The rotary part 150 is connected to the C-arm 130, such that the C-arm 130 is rotated about a rotation axis A1 of the rotary part 150. Therefore, the X-ray tube 160 received in the C-arm 130 is also rotated, such that the focal spot of the X-ray emitted from the X-ray tube is also moved. As illustrated in FIG. 1, the X-ray detector 110 and the compression paddle 120 are moved and/or rotated together by the rotation of the C-arm 130 because the X-ray detector 110 and the compression paddle 120 are connected to the C-arm 130. However, in another exemplary embodiment, the X-ray detector 110 and the compression paddle 120 may be fixed without being affected by the rotation of the C-arm 130. As necessary, only the X-ray detector 110 and the X-ray tube 160 may be rotated except for the compression paddle 120, the breast U, and the outer part (e.g., the bucky) of the X-ray detector 110 that supports the breast U. The rotations of the respective components may be designed such that the respective components may be selectively rotated, or the rotations of the respective components may be designed to be controlled by converting modes (manual or automatic mode). However, the present invention is not limited to coupling relationships between the components or a method of coupling the components.

FIG. 4 is a view illustrating a method of acquiring projection images in a general breast tomosynthesis system. The X-ray tube received in the C-arm is moved at a predetermined speed and in a predetermined direction by the rotation of the C-arm. The dotted lines in FIG. 4 indicate the emitted X-rays. The general breast tomosynthesis system acquires projection images at every predetermined point in time, and a three-dimensional image is implemented based on the plurality of projection images acquired at various angles.

However, because the X-ray tube continues to move while the breast tomosynthesis system in the related art acquires the projection images, actual effective focal spots may vary. In other words, because the movement of the X-ray tube is accompanied by the movement of the focal spot, blurring occurs in the projection image to the extent that the focal spot is moved.

FIG. 5 illustrates the above-mentioned problem in the related art. As illustrated in FIG. 5, as the X-ray tube 3 moves, the focal spot moves from a position FS_t1 at time t1 to a position FS_t3 at time t3. In the projection image acquired in this manner, an actual length of the focal spot is a distance ΔFS between FS_t1 and FS_t3. In this case, when the focal spot moves when one projection image is acquired, blurring occurs due to the movement of the focal spot while capturing the image of the breast U between the X-ray detector 110 and the compression paddle 120.

The digital breast tomosynthesis system 100 according to the present invention uses a focal spot controller 170 to enable a spatial position of the focal spot FS of the X-ray tube 160 to be placed at a predetermined position. That is, from the viewpoint of the X-ray detector 110, the focal spot FS appears to be fixed even while the X-ray tube 160 moves. This configuration may prevent the occurrence of blurring because the actual length of the focal spot is not increased by the movement of the X-ray tube 160 and the actual length of the focal spot is maintained to be equal to the focal spot FS of the X-ray tube 160 may be maintained constantly.

The focal spot controller 170 of the digital breast tomosynthesis system 100 according to the present invention controls the position of the focal spot FS with various methods.

First Exemplary Embodiment

FIGS. 6 and 7 illustrate a method of controlling the position of the focal spot FS of the X-ray tube. The X-ray tube 160 moves from the left side to the right side based on the drawing from time t1 to time t3 for which one projection image is acquired (in more detail, the X-ray tube 160 is moved, by the rotational motion of the C-arm 130, clockwise on a circumference having, at a center thereof, the rotation axis A1 of the C-arm 130). In order to control the focal spot FS of the X-ray tube 160, the focal spot controller 170 controls the position of the focal spot FS by rotating the X-ray tube 160 by a predetermined angle about a rotation axis A2 in the X-ray tube 160.

In this case, the rotation of the X-ray tube 160 by the focal spot controller 170 may be implemented by a mechanical means. That is, the digital breast tomosynthesis system 100 according to the present invention may further include the mechanical means for rotating the X-ray tube 160 illustrated in FIG. 3 about the rotation axis A2. The mechanical means may include a component such as a bearing and a motor for performing the rotation, but the present invention is not limited thereto. The focal spot controller 170 controls the mechanical means based on information about the rotation/movement of the C-arm 130, thereby rotating the X-ray tube 160.

First, at time t1, the focal spot controller 170 moves the X-ray tube 160 counterclockwise by a predetermined angle θ so that the position of the focal spot FS moves in a traveling direction of the X-ray tube 160.

Thereafter, in response to the movement of the X-ray tube 160, the focal spot controller 170, at time t2, moves the X-ray tube 160 clockwise by the predetermined angle θ so that the position of the focal spot FS moves in a direction opposite to the traveling direction of the X-ray tube 160.

Next, the X-ray tube 160 continues to move, and at time t3, the focal spot controller 170 moves the X-ray tube 160 counterclockwise by the predetermined angle θ so that the position of the focal spot FS moves again in the traveling direction of the X-ray tube 160.

Therefore, as illustrated in FIG. 7, the X-ray tube 160 continues to be moved by the C-arm 130 within the section from t1 to t3 for which one projection image is acquired, but the focal spot FS is fixed on a lateral surface of the X-ray detector 110 by the focal spot control of the focal spot controller 170. In other words, a size of a focal spot of an X-ray, which is used to acquire an image, is equal or similar to a size of the X-ray tube 160, such that blurring may be minimized.

Meanwhile, when the focal spot controller 170 controls the movement of the focal spot FS, a rotation angle (the predetermined angle θ in FIG. 6), at which the spatial position of the focal spot FS based on the X-ray detector 110 is fixed, needs to be calculated based on a rotational speed of the C-arm 130 (i.e., a movement speed of the X-ray tube 160).

For example, assuming that a scanning angle is 20°, exposure time is 100 msec, and rotation time is 10 seconds, a movement distance of the focal spot FS at the moment when the projection image is acquired, is approximately 2.27 mm. In this case, a total movement distance of the X-ray tube 160 is approximately 227 mm, and a movement speed per second is 22.7 mm/sec. The movement distance for 100 msec is 2.27 mm, and when the focal spot FS is spaced apart from the rotation axis A2 in the X-ray tube 160 by 34 mm, an appropriate rotation angle of the X-ray tube 160 for moving the focal spot FS by 2.27 mm is approximately 3.82°. That is, the focal spot controller 170 may fix the spatial position of the focal spot FS based on the X-ray detector 110 by rotating the X-ray tube 160 by approximately 4.225°.

Second Exemplary Embodiment

FIG. 8 illustrates another method of controlling the position of the focal spot FS of the X-ray tube 160. In order to fix the spatial position of the focal spot FS based on the X-ray detector 110, the focal spot controller 170 moves the X-ray tube 160 in a second direction opposite to a first direction which is the movement direction of the X-ray tube 160 (i.e., the movement of the focal spot FS), such that the spatial position of the focal spot FS based on the X-ray detector 110 is fixed, thereby achieving the effect identical to the effect illustrated in FIG. 7.

In this case, the first direction means the direction in which the X-ray tube 160 is moved by the C-arm 130 that rotates based on the rotation axis A1, and the second direction means the direction opposite to the first direction. That is, the first direction is a clockwise direction about the rotation axis A1, and the second direction is a counterclockwise direction about the rotation axis A1.

In this case, the rotation or movement in the second direction of the X-ray tube 160 by the focal spot controller 170 may be implemented by a mechanical means. That is, the digital breast tomosynthesis system 100 according to the present invention may further include the mechanical means for moving the X-ray tube 160 in the second direction. The focal spot controller 170 achieves the movement in the second direction of the X-ray tube 160 by controlling the mechanical means based on information about the rotation/movement of the C-arm 130. In other words, the focal spot controller achieves the rotation in the second direction about the rotation axis A1.

For example, assuming that a scanning angle is 20°, exposure time is 100 msec, and rotation time is 10 seconds, a movement distance of the focal spot FS is approximately 2.27 mm. In this case, a total movement distance of the X-ray tube 160 is approximately 227 mm, and a movement speed per second is 22.7 mm/sec. A movement distance for 100 msec is 2.27 mm. That is, the focal spot controller 170 may fix the spatial position of the focal spot FS based on the X-ray detector 110 by moving the X-ray tube 160 for 100 msec in the second movement direction by approximately 2.27 mm.

Third Exemplary Embodiment

FIG. 9 illustrates still another method of controlling the position of the focal spot FS of the X-ray tube 160. In order to fix the spatial position of the focal spot FS based on the X-ray detector 110, the focal spot controller 170 rotates the X-ray tube 160 about the rotation axis A3 to move the focal spot FS in the second direction opposite to the first direction which is the movement direction of the X-ray tube 160, thereby achieving the effect identical to the effect illustrated in FIG. 7.

In this case, a rotation axis A3 about which the X-ray tube 160 rotates may be positioned inside or outside a circumference having, at a center thereof, the rotation axis A1 of the C-arm 130 and having a radius which is a distance between the rotation axis A1 and the X-ray tube 130.

In this case, the first direction means the direction in which the X-ray tube 160 is moved by the C-arm 130 that rotates based on the central axis A1, and the second direction means the direction opposite to the first direction. That is, the first direction is a clockwise direction about the central axis A1, and the second direction is a counterclockwise direction about the central axis A1.

In this case, the rotation of the X-ray tube 160 about the rotation axis A3 by the focal spot controller 170 may be implemented by the mechanical means. That is, the digital breast tomosynthesis system 100 according to the present invention may further include the mechanical means for rotating the X-ray tube 160 about the rotation axis A3. The focal spot controller 170 may control the mechanical means based on information about the rotation/movement of the C-arm 130 to rotate the X-ray tube 160 in the second direction about the rotation axis A3, thereby moving the focal spot FS in the second direction. With the above-mentioned implementation method, it is possible to effectively fix the focal spot of the X-ray with smaller force in comparison with the second exemplary embodiment.

The features, structures, and effects described in each of the above-mentioned exemplary embodiments are included in one exemplary embodiment of the present invention, but the present invention is not necessarily limited to the exemplary embodiment. Furthermore, the features, structures, and effects described in each of the exemplary embodiments may be combined, altered, changed, converted, replaced, added, modified, and applied by those skilled in the art to which the present invention pertains. Accordingly, the combination, the alteration, the change, the conversion, the replacement, the addition, and the modification may also be construed as being included in the scope of the present invention without departing from the technical spirit defined in the appended claims.

INDUSTRIAL APPLICABILITY

According to the digital breast tomosynthesis system having the above-mentioned configuration, the position of the focal spot of the X-ray tube may be controlled by the simple structure and method, thereby eliminating blurring of a projection image that affects the determination of quality of a three-dimensional image, and thus significantly improving sharpness.

The invention claimed is:

1. A digital breast tomosynthesis system comprising:
an X-ray tube configured to generate X-rays;
a C-arm configured to receive the X-ray tube and rotate about a first rotation axis during an X-ray exposure period;
an X-ray detector configured to convert the X-ray, which is emitted from the X-ray tube and passes through a breast, into image information; and
a focal spot controller configured to operate in conjunction with a movement of the X-ray tube caused by a rotation of the C-arm, the focal spot controller being configured to control a position of a focal spot of the X-ray by rotating the X-ray tube about a second rotation axis in the C-arm.

2. The digital breast tomosynthesis system of claim 1, wherein as a position of the focal spot is moved in a direction opposite to a movement direction of the X-ray tube by the rotation about the second rotation axis, a spatial position of the focal spot based on the X-ray detector is fixed.

3. The digital breast tomosynthesis system of claim 1, wherein the focal spot controller calculates a rotation angle, at which a spatial position of the focal spot is fixed, based on a movement speed of the X-ray tube, and rotates the X-ray tube based on the calculated rotation angle.

4. The digital breast tomosynthesis system of claim 1, wherein the second rotation axis is positioned on a circumference having, at a center thereof, the first rotation axis and having a radius which is a distance between the first rotation axis and the X-ray tube.

5. The digital breast tomosynthesis system of claim 1, wherein the focal spot controller controls and fixes a spatial position of the focal spot by rotating the X-ray tube so that the focal spot is advanced from a predetermined position based on a movement direction of the X-ray tube, and then by rotating the X-ray tube again in the opposite direction.

6. A digital breast tomosynthesis system comprising:
an X-ray tube configured to generate X-rays;
a C-arm configured to receive the X-ray tube and rotate about a first rotation axis during an X-ray exposure period;
an X-ray detector configured to convert the X-ray, which is emitted from the X-ray tube and passes through a breast, into image information; and
a focal spot controller configured to control a position of a focal spot of the X-ray by moving the X-ray tube, which moves in a first direction along a circumference having, at a center thereof, the first rotation axis, in a second direction opposite to the first direction.

7. The digital breast tomosynthesis system of claim 6, wherein the focal spot controller fixes a spatial position of the focal spot based on the X-ray detector by moving the focal spot in the second direction.

8. A digital breast tomosynthesis system comprising:
an X-ray tube configured to generate X-rays;
a C-arm configured to receive the X-ray tube and rotate about a first rotation axis during an X-ray exposure period;
an X-ray detector configured to convert the X-ray, which is emitted from the X-ray tube and passes through a breast, into image information; and
a focal spot controller configured to operate in conjunction with a movement of the X-ray tube caused by a rotation of the C-arm, the focal spot controller being configured to control a position of a focal spot of the X-ray by rotating the X-ray tube about a third rotation axis,
wherein the third rotation axis is positioned inside or outside a circumference having, at a center thereof, the first rotation axis and having a radius which is a distance between the first rotation axis and the X-ray tube.

9. The digital breast tomosynthesis system of claim 8, wherein the focal spot controller fixes a spatial position of the focal spot based on the X-ray detector by rotating the focal spot about the third rotation axis.

* * * * *